US005503152A

United States Patent [19]
Oakley et al.

[11] Patent Number: 5,503,152
[45] Date of Patent: Apr. 2, 1996

[54] ULTRASONIC TRANSDUCER ASSEMBLY AND METHOD FOR THREE-DIMENSIONAL IMAGING

[75] Inventors: Clyde G. Oakley, Englewood; Lawrence J. Busse, Littleton, both of Colo.

[73] Assignee: Tetrad Corporation, Englewood, Colo.

[21] Appl. No.: 314,424

[22] Filed: Sep. 28, 1994

[51] Int. Cl.[6] .................................................. A61B 8/00
[52] U.S. Cl. ..................... 128/661.01; 128/916; 73/626
[58] Field of Search ........................ 128/660.07, 660.08, 128/661.01, 916; 73/626

[56] References Cited

U.S. PATENT DOCUMENTS

| | | |
|---|---|---|
| Re. 30,397 | 9/1980 | King . |
| 3,156,110 | 11/1964 | Clynes . |
| 4,028,934 | 6/1977 | Sollish . |
| 4,097,835 | 6/1978 | Green . |
| 4,100,916 | 7/1978 | King . |
| 4,733,562 | 3/1988 | Saugeon . |
| 4,747,411 | 5/1988 | Ledley . |
| 4,787,394 | 11/1988 | Ogura . |
| 4,821,728 | 4/1989 | Ledley . |
| 4,846,186 | 7/1989 | Yoshioka . |
| 4,924,869 | 5/1990 | Takeuchi et al. . |
| 5,050,611 | 9/1991 | Takamizawa et al. . |
| 5,090,411 | 2/1992 | Higuchi . |
| 5,186,175 | 2/1993 | Hirama et al. . |
| 5,269,307 | 12/1993 | Fife et al. . |
| 5,305,756 | 4/1994 | Entrekin et al. . |
| 5,365,929 | 11/1994 | Peterson .................................. 128/916 |
| 5,396,890 | 3/1995 | Weng ....................................... 128/916 |

OTHER PUBLICATIONS

Howry et al "Three-Dimensional . . . " *J. Appl. Physiology* 9, 304–6 Henderson A Stereo Sonar . . . 1992 *IEEE Ultrasonic Symposium*, 1151–54.
Smith et al "High-Speed Ultrasound . . . " 1991 *IEEE Trans. on Ultrasonics, Ferroelectrics, and Frequency Control*, 38, No. 2, 110–108.
von Ramm et al "High-Speed Ultrasound . . . " *id.* at 109–115 Entrekin et al Real–time 3–D . . . *SPIE* v. 1733, 264–272.

*Primary Examiner*—George Manuel
*Attorney, Agent, or Firm*—Michael de Angeli

[57] ABSTRACT

Elongated arrays of individual ultrasonic transducer elements at spaced locations emit wedge-shaped beams of ultrasonic energy such that energy emitted by corresponding elements of the arrays travels into a common region of the object to be imaged. Energy emitted by the elements of both arrays is reflected by the same structure within the object. The relative distances of the reflecting structure from the corresponding elements of the arrays are compared to determine the elevation of the reflecting points with respect to an image plane, and a three-dimensional image of the reflectors is generated. A virtual image including information responsive to the elevation of the points can be derived, and used to recalculate the visible display corresponding to a user-selected image plane. The transducer may include a parallel pair of arrays.

56 Claims, 5 Drawing Sheets

ULTRASONIC TRANSDUCER ASSEMBLY AND METHOD FOR THREE-DIMENSIONAL IMAGING

GOVERNMENT INTEREST

This invention was made with government support under Grant No. HL44230 awarded by the National Institutes of Health. The government has certain rights in the invention.

FIELD OF THE INVENTION

This invention relates to improved methods and accompanying apparatus for three-dimensional ultrasonic imaging of the interior of an object, such as the internal organs of a patient.

BACKGROUND OF THE INVENTION

Ultrasonic imaging is commonly performed to provide an image of structure internal to an object. For example, it is common to perform ultrasonic examination, e.g., of pregnant women by disposing a multiple-element ultrasonic transducer against the abdomen and sequentially exciting the elements of the transducer. Pulses of ultrasonic energy are then transmitted inwardly, and are reflected at interfaces between structures of differing acoustic impedance. The reflected energy is detected by the transducer elements, which then provide electrical signals responsive to the detected energy. These signals can be processed to yield a visible image of the interfaces, that is, of the outlines of various structures within the abdomen.

Ultrasonic examination is also commonly carried out endoscopically, that is, using transducers mounted on probes inserted into the patient's body through a naturally occurring or surgically formed portal so as to be juxtaposed to an organ or other structure of interest. Ultrasonic examination is also performed in industrial applications, e.g., for non-destructive examination of manufactured products and the like.

A number of scanning and image display techniques have become generally standardized. These include the "A-scan", wherein a focused or "pencil" beam is directed into the object of interest. The reflected energy, that is, "echoes" are detected and displayed, by a "trace" plotting the amplitude of the received energy signal on the vertical axis and time after transmission on the horizontal axis, such that the distance of features in the trace from one edge of the display indicates the relative depth of the reflecting interfaces. To provide three-dimensional information describing internal structure using the A-scan technique requires performing such examinations at spaced locations along a number of generally parallel lines, and mentally interpolating the results; this process is too difficult for most practitioners.

The A-scan process has been largely supplanted by the "B-scan" technique, wherein a two-dimensional image, i.e., an image of a cross-sectional "slice" is formed An elongated multiple-element transducer is commonly used to provide a series of parallel "pencil" beams focused by sequential addressing or phase-steering techniques. A focused beam may also be physically steered. "Lines" corresponding to energy reflected from structure along the path of successive pencil beams extending into a particular portion of the object are displayed side-by-side, while the brightness of the display is varied responsive to the strength of the reflected signal. The images formed each correspond to a cross-sectional view or two-dimensional "slice" extending into the object to be imaged. If the transducer is moved slowly along a line perpendicular to the image plane while a sequence of such images is formed, one can mentally interpolate changes in the shapes of the interfaces, that is, in order to obtain a three-dimensional mental image. Although this technique is workable for highly-skilled practitioners, clearly it would be desirable to provide a true three-dimensional image, capable of being recorded or displayed to others. Moreover, a three-dimensional image would be highly useful in determining the position of an implement, e.g., monitoring the motion of a biopsy needle approaching a tumor.

The prior art suggests several techniques for providing a three-dimensional image employing ultrasonic energy. For example, see U.S. Pat. Nos. 4,747,411 and 4,821,728 to Ledley, disclosing the "reconstruction" of three-dimensional information by automated comparison of two-dimensional "slices" extending into the object. The reconstructed information is used to generate two images exhibiting relative parallax corresponding to the two images formed by one's eyes, that is, with foreground objects being displaced from one another in the two images by a greater amount than background objects. The two images may be displayed side-by-side for simultaneous stereoscopic viewing, for example, on adjoining video screens, as disclosed by Ledley, or may be displayed alternatingly on a single screen, together with means for ensuring that each of the viewer's eyes "sees" only the corresponding image. For example, the image intended for one eye may be polarized in a first sense, and that intended for the other eye polarized in the opposite sense, and the viewer provided with "eyeglasses" fitted with corresponding polarizing filters. A substantially similar effect can be achieved using differential coloring of the two images and colored filters.

The prior art has typically generated such pairs of images for three-dimensional display by forming two images using ultrasonic sources and detectors at spaced viewpoints, that is, corresponding to the viewer's eyepoints. See the Ledley '411 patent at col. 5, lines 51–55. This is, of course, the intuitive first approach to the problem of providing three-dimensional images. However, there are numerous deficiencies to such an approach, one being that the image displayed is constrained to represent objects being imaged as if seen from a viewing location corresponding to the actual location of the sources and detectors of the ultrasonic energy. In many circumstances the transducer is constrained by anatomy from being placed at a distance from the structure to be imaged suitable for normal viewing. Furthermore, as acknowledged by Ledley, the number of sources and detectors that can be employed in a given scanning plane is limited, reducing the effective signal-to-noise ratio.

Ledley suggests (col. 6, lines 16–42) that the same result can be obtained using a single source/detector pair swept physically through a plurality of angles and processing the returned signals to "develop data representing forward projections of the object . . . onto [the] image plane . . . ". However, this arrangement would also seem to suffer the disadvantages mentioned above, and would further require a mechanical device to provide the scanning motion. The latter not only involves additional complexity and expense, but also requires that a number of images be formed over a period of time; this imposes the requirement that the object be stationary, precluding imaging of a living heart, for example.

Other prior art patents generally relevant to the subject matter of this invention include U.S. Pat. No. 4,028,934 to Sollish, showing two mechanically scanned cylindrically focused elongated transducers used to form images with respect to image planes forming an angle to one another. See FIGS. 6 and 7. The two images are used to provide a perspective view rather than cross-sectional tomograms. See FIG. 3. The images are displayed on two screens or slides and viewed stereoscopically. Sollish also suggests that a number of B-scan images can be processed to provide a holograph displaying three-dimensional information, although this process would be time-consuming and impractical.

A number of patents, including U.S. Pat. No. 4,097,835 to Green, U.S. Pat. No. 4,924,869 to Takeuchi et al, U.S. Pat. No. 5,090,411 to Higuchi, and U.S. Pat. No. 5,050,611 to Takamizawa et al, show simultaneously generating Doppler blood flow data together with B-scan tomographic information. The Green patent shows semi-circular piezoelectric transducers with focusing elements moved in opposite directions along parallel linear paths.

U.S. Pat. No. 5,186,175 to Hirama et al. shows a system wherein a large number of transducers are arranged in lateral and azimuth directions to form a two-dimensional array.

U.S. Pat. No. 4,100,916 to King, which was reissued as Re. 30,397, shows an apparatus for three-dimensional ultrasonic imaging in which electrical sparks are used to provide the ultrasonic energy. The system is used only external to a body structure to be imaged.

U.S. Pat. No. 4,846,188 to Yoshioka shows a system wherein images synchronized to a patient's heart beat are sequentially collected, evidently to provide a "movie" of images.

U.S. Pat. No. 4,787,394 to Ogura shows a system wherein two ultrasonic transducers are used to form two tomograms to monitor the destruction of a calculus such as a kidney stone, using a third beam emitter as the source of destructive energy.

U.S. Pat. No. 4,733,562 to Saugeon shows an ultrasonic array divided into subarrays for providing a steered ultrasonic beam.

Finally, U.S. Pat. No. 3,156,110 to Clynes shows generation of energy at three different ultrasonic frequencies for reflection from different sorts of structures within the body.

Most prior art directed to ultrasonic imaging has attempted to image as thin as possible a cross-sectional "slice" through the structure of interest, as the thickness of the slice limits the resolution of the image. The usual "B-scan" ultrasonic imaging techniques employed require many such images to be formed and mentally interpolated in order to convey three-dimensional information. The Ledley patents attempt to eliminate the necessity of mentally interpolating a series of "slices" by reconstructing the slices to generate images exhibiting parallax for stereoscopic display. However, the Ledley approach introduces further difficulties, as noted above. Furthermore, if a particular feature of the structure does not happen to coincide with any of the slices, that feature will be omitted entirely from the image. It would be highly preferable to provide a three-dimensional image of an entire volume of an object of interest.

Howry et al, "Three-Dimensional and Stereoscopic Observation of Body Structures by Ultrasound" *J. Appl. Physiology* 9, 304–6, (1956), proposes stereoscopic viewing of two 'pictures', each comprising a sum of a number of cross-sectional views of an object formed using ultrasonic techniques. The cross-sectional views making up each picture are formed sequentially, by moving a transducer along a vertical line perpendicular to a line connecting the transducer and the object. The cross-sectional views thus formed at each position of the transducer along a first line are simultaneously displayed, and are effectively summed to form the first of the pictures. Each of the views being summed is displayed with gradually varying vertical scale, such that the summed picture effectively corresponds to a perspective view. A second set of similarly formed views from transducer locations extending along a second vertical line spaced from the first is then formed and summed similarly. The two pictures are then displayed side-by-side for stereoscopic viewing, such that parallax in the two pictures yields a three-dimensional image.

Henderson, "A Stereo Sonar for Object Examination" 1992 *IEEE, Ultrasonics Symposium,* 1151–54, discusses a method of displaying two sonar images for exhibiting three-dimensional information. An elongated multiple-element transducer arranged transverse to a line connecting the transducer and the object is employed to form first and second sonar images at a single location; the transducer is tilted typically through 10°, after formation of the first image Both images include energy reflected from reflecting surfaces on the half of the object toward the transducer as if seen from above, such that reflecting surfaces on the upper and lower portions of the object overlap in each image. The images are displayed for stereoscopic viewing, that is, each image is "seen" by one of the viewer's eyes. Parallax in the two images allows the viewer to synthesize the depth information and separate reflectors on the upper and lower surfaces of the object.

Smith et al, "High-Speed Ultrasound Volumetric Imaging System— Part I: Transducer Design and Beam Steering" *IEEE Trans. on Ultrasonics, Ferroelectrics and Frequency Control,* 38, No. 2, 100–108 (1991) and von Ramm et al, "High-Speed Ultrasound Volumetric Imaging System—Part II: Parallel Processing and Image Display", id. at 109–115, disclose a system for three—dimensional ultrasonic imaging wherein a two-dimensional, planar array of transducer elements is used to transmit ultrasonic energy into a generally pyramidal volume of an object to be imaged. Energy reflected from structure at given depths from the transducer array in the volume is imaged in a similar pattern, such that the display is of a cross-section parallel to the surface of the object. If two images taken at relatively spaced or angled viewpoints are displayed for stereoscopic viewing, 3-D relationships may be perceived. A number of differing methods of conveying 3-D information to the viewer are disclosed at 113–14, including alternating display of stereoscopic images on a single display, using polarization techniques to ensure that each of the viewer's eyes sees the only the appropriate image, or by color-coding energy reflected from different depths in the volume.

Entrekin et al, "Real-time 3-D ultrasound imaging with a 1-D 'fan beam' transducer array", *SPIE* V. 1733, 264–272 (1992), and Entrekin et al. U.S. Pat. No. 5,305,756 refer to the results of Smith et al. and von Ramm et al. discussed above, but disclose modification of a conventional elongated, multiple-element (i.e. "1-D") transducer array as used for linear or phased-array B-scan ultrasonic examination. Conventionally, in order to provide a narrow beam and improve the resolution of the image, a transducer array is employed with a convex RTV silicone rubber lens over the active surface of the transducer array; as the speed of sound in RTV rubber is slower than in tissue, this array/lens combination provides a collimated beam in elevation, i.e., one that is narrow in the plane including the axis of elongation of the array. Such a transducer may be rotated about its axis through an angle of typically 60° to form a conventional 2-D image; that is, the reflected energy detected at each of a plurality of angularly-spaced positions of the transducer is displayed line-by-line to form the B-scan image.

According to the modification disclosed by Entrekin et al, the narrow beam conventionally provided is replaced with a beam diverging in elevation, so that a wedge-shaped volume of the object, with the apex of the wedge extending along the surface of the transducer array, is illuminated with ultrasonic energy. An image is then formed as in the conventional B-scan technique, except that each line of the image includes energy reflected from structure within the corresponding wedge-shaped volume. The wedge-shaped beam may be provided by replacing the conventional convex RTV rubber lens by a concave lens of the same material, so that the beam diverges in elevation, by forming the transducer with a convex outer surface, or by electronically forming a diverging beam using a two-dimensional transducer array. See col. 5, line 54 through col. 6, line 29 of the Entrekin et al. patent.

Images included in the Entrekin et al. paper illustrate that a quasi-3-D effect is provided. However, as acknowledged by Entrekin et al. (see "5. Discussion"), their method has several significant limitations. Chief among these is the fact that all reflectors at the same range in elevation are superposed in the display, rendering the actual location of the reflectors ambiguous. Where the object is in motion, this ambiguity can be resolved by the eye of the viewer. However, in many circumstances, this fact limits the utility of the Entrekin et al. system to imaging the surfaces of objects surrounded by fluid.

OBJECTS OF THE INVENTION

It is accordingly an object of the invention to provide a method and apparatus for forming three-dimensional images of the interior of objects such as organs and the like employing ultrasonic energy, wherein the images are not constrained to be displayed as if the viewer's eyes were disposed in the same relationship to the structure imaged as borne by the transducer to the structure being imaged.

A further object of the invention is to provide a method and apparatus for forming three-dimensional images of the interior of organs and the like employing ultrasonic energy, wherein a three-dimensional image can be formed in real time, that is, without the necessity of moving the transducer between different locations with respect to the structure to be imaged.

A further object of the invention is to provide a method and apparatus for forming three-dimensional images of the interior of organs and the like employing ultrasonic energy, wherein an entire region of the object of interest is imaged, as compared to the prior art technique of forming images by reconstructing data corresponding to a number of discrete slices through the object.

SUMMARY OF THE INVENTION

The present invention satisfies the needs of the art and the objects of the invention mentioned above by provision of novel ultrasonic transducer assemblies and novel methods of forming three-dimensional images of the interior of an object. Ultrasonic energy is transmitted into an object to be imaged from two or more spaced locations; structure within the object reflects ultrasonic energy, as detected by transducer elements at the same or different spaced locations. The location of the reflecting structure is determined by comparison of the energy detected by the transducer elements at the spaced locations, and used to provide a visible image displaying three-dimensional information.

In a preferred embodiment, the transducer assembly comprises a pair of elongated arrays of individual transducer elements for simultaneous ultrasonic imaging of a common volume of the object to be imaged from spaced locations without the necessity of moving the transducer between the spaced locations. However, the invention can be implemented such that the same volume of the object is ultrasonically examined by a single transducer array disposed at first and second locations, that is, wherein the same volume is imaged at two different times, or by other transducer arrangements.

In a particularly preferred embodiment, the integrated transducer assembly may comprise a parallel pair of elongated arrays of elements, each emitting ultrasonic energy in a diverging, "wedge"-shaped beam pattern. When corresponding elements of the pair of arrays are supplied with a suitable drive signal, pulses of ultrasonic energy travel from each transducer array into a common, i.e., overlapping, region of the object to be imaged. Accordingly, energy emitted by elements of both arrays is reflected by the same structure—that is, at the same acoustic interface—within the object, and is detected separately by elements on each of the two arrays.

The relative distances of common reflecting points on the interfaces from the corresponding elements of the two arrays are compared to determine the elevation of those points with respect to an image plane, that is, by triangulation. Where the arrays are parallel, the image plane may extend between the transducer arrays. A visible image including information responsive to the elevation of the points with respect to the image plane, that is, three-dimensional information, is then generated and displayed.

The visible image may include two images including relative parallax and arranged for simultaneous stereoscopic viewing, or for alternating display on a single display device, with means provided so that each of the eyes of the viewer "sees" only the appropriate one of the images. For example, the images may be differently polarized, and the viewer provided with crossed-polarizer eyeglasses. Alternatively, shutters may be provided for each eye, synchronized to the alternatingly-displayed images.

In a further alternative, a single image can be displayed wherein the elevation information is provided using visual "clues"— for example, foreground objects may be displayed more brightly or outlined more heavily than background objects, or may be "false-colored", to provide an indication of their relative elevation with respect to the image plane.

Further according to the invention, the sources and detectors need not lie in or parallel to the plane with respect to which the visible image is generated and displayed, as is usual in the prior art. According to the invention, the effective viewpoint may be located at substantially any desired position with respect to the transducer location. For convenience in image processing operations, specifically in relocation of the effective viewpoint with respect to the transducer location, it may be desirable to generate and store a "virtual image", comprising a three-dimensional array of data describing the position of all reflecting points within the region to be imaged with respect to a predetermined reference image plane. In a preferred embodiment, the reference image plane with respect to which the virtual image is formed extends between the parallel arrays, simplifying the formation of the virtual image, but this is not critical to the invention. The data stored by the virtual image can then be translated to provide a visible image corresponding to any desired image plane. Similarly, while the visible image may conveniently be formed with respect to an image plane extending between the parallel arrays, as above, the visible image may be displayed with respect to any desired image plane by recalculation of the data stored in the virtual image responsive to the relationship between the desired image plane and the arbitrary image plane.

Still further, in certain embodiments of the invention, the process of emitting energy into the object to be examined and detection of reflection of energy therefrom may take place without mechanical movement of the transducer assembly with respect to the object, simplifying and speeding the processing of the reflected energy in order to provide the three-dimensional images in real time.

Further according to the invention, reflectors are detected at any point within the volume of the object being examined into which ultrasonic energy is emitted by the transducer elements, eliminating the possibility of omitting objects not coinciding with a "slice" through the object.

BRIEF DESCRIPTION OF THE DRAWINGS

The invention will be better understood if reference is made to the appended drawings, in which.

DESCRIPTION OF THE PREFERRED EMBODIMENTS

Figures 1, 2:
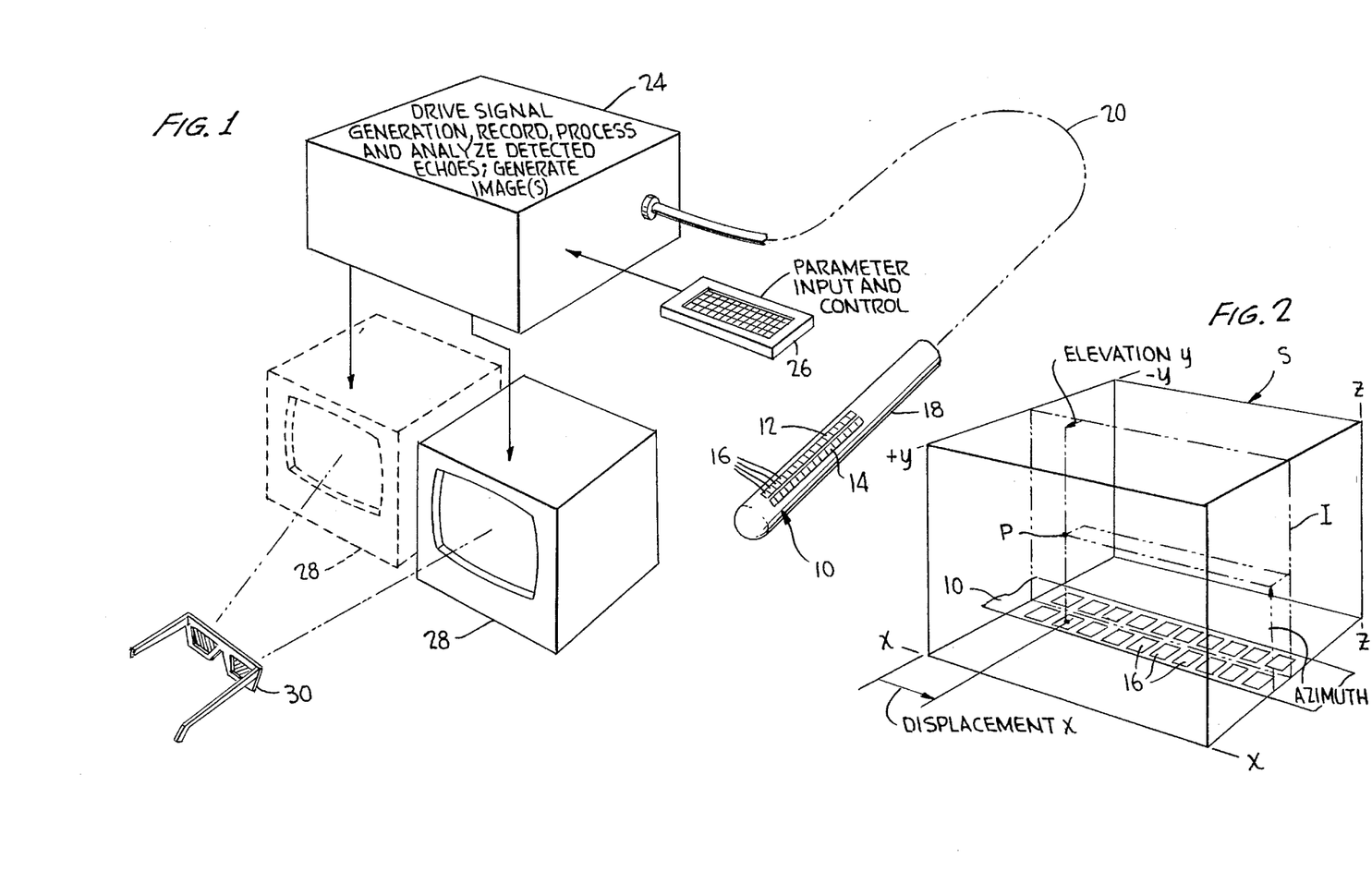
FIG. 1 is an idealized overall view of a system for ultrasonic imaging according to the invention.
FIG. 2 explains certain terminology useful in understanding the invention.

FIG. 1 illustrates the principal components of a system for providing three-dimensional images of the interior structure of objects of interest, such as internal organs of a patient or the like. In this embodiment, an integrated ultrasonic transducer assembly 10 is provided, comprising at least two parallel elongated arrays 12 and 14 of individually excitable transducer elements 16, arranged for convenient juxtaposition to the object to be examined.

Each element of the arrays is arranged as discussed in detail below to emit ultrasonic energy in a generally diverging, "wedge"-shaped pattern, so that any given region of the object to be examined is "illuminated" with energy from elements in each of the arrays. The same effect may be obtained by paired separate transducer arrays, or by disposing a single array at differing positions with respect to the object to be imaged and correlating plural images taken at successive times.

Transducer elements 16 are typically formed of a piezoelectric material, and are configured and operated to emit a beam of ultrasonic energy of desired beam shape (as discussed in detail below) when excited by suitable high-frequency electrical signals. The same elements (or adjoining elements of generally similar material and configuration) provide electrical signals responsive to detection of "echoes" that is responsive to detection of ultrasonic energy after reflection at interfaces between materials of differing acoustic impedance within an object the internal structure of which is to be imaged.

In the embodiment shown, the transducer assembly 10 is disposed at the distal end of an elongated probe 18, e.g., for endoscopic examination of internal organs or the like through a naturally-occurring or surgically-formed portal; however, the transducer assembly 10 may also be employed for external ultrasonic examination, or for nonmedical applications.

Transducer assembly 10 is connected by a multiple-conductor cable 20 to system console equipment shown generally at 24 for providing suitable drive signals to the transducer elements 16, and for suitably amplifying, recording, processing, and analyzing signals responsive to the detected energy. System console equipment 24 may receive user input via keyboard 26, for control of various imaging parameters, such as the drive signal sequence, as well as inputs defining the type of display to be provided, and determining the relative location of the image plane (discussed in detail below) with respect to the transducer assembly 10. System console equipment 24 processes the signals provided by the transducer assembly 10 to derive three-dimensional information describing internal structure of an object of interest, and provides a visible image thereof to one or more display screens 28, or other output devices.

A number of display options are within the scope of the invention. Two display devices 28 may be employed for simultaneous stereoscopic side-by-side viewing of two images conveying three-dimensional information through parallax in the images, or a single screen 28 may be employed for alternating display of these images, in combination with "eyeglasses" 30 for ensuring that each of the viewer's eyes "sees" only the corresponding image, shutters synchronized to the alternating display of the two images, or other means. In a further possibility, a single screen 28 may display a single image, in which three-dimensional information is conveyed by variation of one or more of the display parameters with respect to the elevation of objects appearing in the image with respect to an image plane. After discussion of the method of the invention of deriving three-dimensional information concerning internal structure of an object of interest, each of these display possibilities is addressed below in detail.

FIG. 2 illustrates terminology useful in understanding the invention. In the example shown, suppose that a transducer assembly 10 according to the invention, in this embodiment comprising two parallel elongated arrays of individual elements 16, is disposed beneath a particular volume S of an object the internal structure of which is to be imaged. More specifically, suppose that it is desired to form an image with respect to an image plane I, that is, the image is to be formed with respect to an effective viewpoint perpendicular to I and spaced some distance therefrom. The image is to depict interfaces between material of varying acoustic impedance as may occur throughout S, as exemplified by a solid particle P. In this example, image plane I extends between the parallel arrays of transducer elements 16, but this is not necessarily the case.

The perpendicular distance of any particular point, e.g., P, within S from the image plane I is referred to as the "elevation" y of P. With image plane I located as shown between the arrays of elements 16, y may be positive or negative, i.e., P can be on either side of I. The perpendicular distance of P from a plane including the left edge of region S is termed its "displacement" x, and its perpendicular distance from a plane including the lower edge of S as its "azimuth" z. In the arrangement shown, x and z are both positive for all positions of P. The location of any point P within S can be specified by these three quantities; more particularly, in order to locate the interfaces between materials of differing acoustic impedance within S to be depicted in order to provide an accurate image of the structure within S, it is essential to locate points on the interfaces by these three quantities. FIGS. 3–8 explain how this is accomplished according to the invention.

Figures 3, 4, 5:
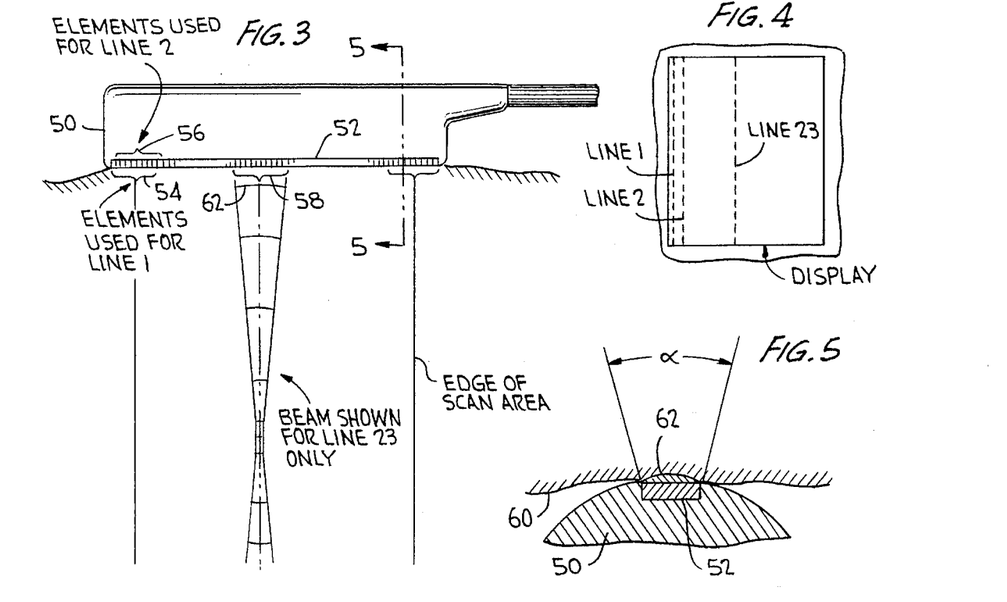
FIG. 3 is a side view of a linear sequenced array transducer, illustrating the manner whereby focused beams of ultrasonic energy are transmitted.
FIG. 4 illustrates the formation of an image corresponding to FIG. 3.
FIG. 5 is a cross-section taken transversely through a transducer element according to the invention.
Figure 6:
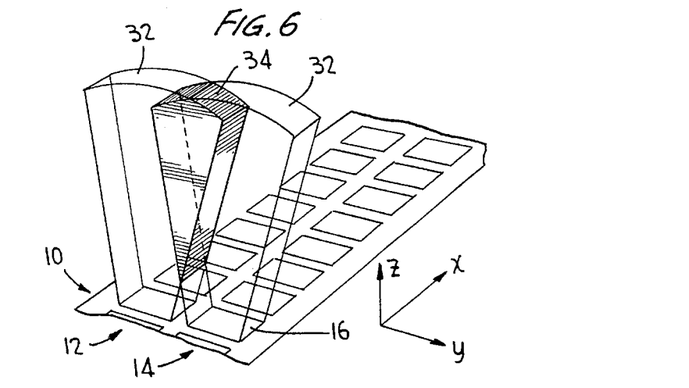
FIG. 6 is a perspective view showing the shape of the overlapping beams of ultrasonic energy emitted by the transducer elements in one embodiment of the invention.
Figure 7:
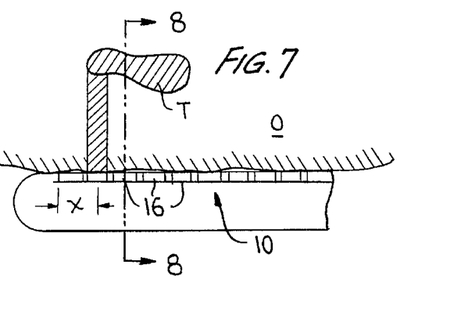
FIG. 7 is a schematic view of the transducer assembly of FIG. 6, taken parallel to a preferred image plane.
Figure 8:
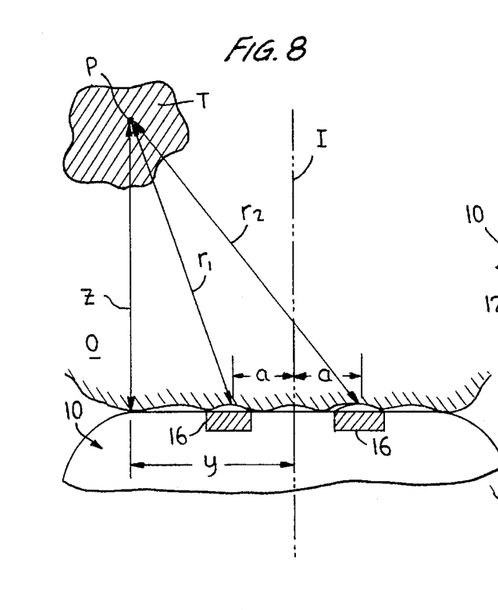
FIG. 8 is a schematic view of the transducer assembly of FIG. 6, taken perpendicular to the view of FIG. 7.

FIG. 3 shows how the beams emitted from each of a number of subsets of an array of transducers are focused at a particular depth within a volume of an object to be imaged. FIG. 4 illustrates the manner in which the reflected energy is displayed to form an image. FIG. 5 illustrates the configuration of and the beam emitted by a typical transducer element and lens combination according to the invention. FIGS. 6, 7, and 8 illustrate the use of such beams as emitted by two arrays of transducer elements to locate a point P in three dimensions according to the invention.

FIG. 3 shows a multiple-element linear sequenced array transducer 50 in side view. The transducer 50 comprises, in this example, approximately fifty individually actuatable transducer elements 52 arranged along a line. One such element is shown in cross-section in FIG. 5. Successive subsets of the elements 52 as indicated by brackets 54, 56, 58 are "fired"—that is, emit pulses of ultrasonic energy responsive to supply of suitable high-frequency drive signals thereto—to image structure along a corresponding "line" in the object to be imaged. For example, the elements 52 in bracket 54, starting with the distal element, are employed to form line 1, that is, to form the beam defining the distal edge of the scanned volume. Energy reflected from structure within the object is detected by the same elements and processed to form the leftmost portion, referred to as "line 1", of the display. See FIG. 4. After line 1 has been thus formed, the subset of elements 52 indicated by bracket 56 are used similarly to form line 2, and so on across the width of the transducer and the corresponding width of the display.

FIG. 3 also illustrates the focusing of the beam, using line 23 of the image as an example. In the plane of FIG. 3, the beams emitted by the subsets of elements 52 are effectively focused in response to the timing of the "firing" of the elements of each subset of elements; that is, high frequency energy is supplied to the elements at controllably sequenced respective times in order to direct a focused beam into an object to be imaged. As indicated, the beam is shaped to form a "waist" that is to be effectively focused at a point some distance from the transducer array. In a typical medical application, the beam is controlled to be focused between 3 and 12 cm from the array, depending on the particular needs of the operator.

Focusing of the ultrasonic beam is accomplished by sequentially firing the individual elements 52 of the subset of elements, e.g., the elements 52 bracketed at 58 are used to form line 23 of the image. More particularly, where the beam is to be focused symmetrically about its centerline as in FIG. 3, the individual elements 52 at either end of the bracketed group 58 are fired first; their immediately inward neighbors are fired next, followed by the next pair, and so on, such that the center or pair of center transducer elements 52 are fired last. Each element emits a spherically diverging wavefront when fired. The wavefronts are summed according to the principle of constructive interference, such that a resultant wavefront 62 of ultrasonic energy travels into the object 60. As the end elements are fired first, the resultant wavefront 62 is curved, as shown. Because the energy has a longer distance to travel from the end elements of the group 58 than from the center, the curved resultant wavefront 62 is effectively flattened and becomes shorter as it travels into the object 60, as shown; the effect is to focus the energy at a focal point spaced from the array.

The focal point is spaced from the array by a distance inversely proportional to the square of the relative time delay between the time of firing of each of the individual elements; that is, if it is desired to focus the energy closer to the array, a greater relative time difference is provided between the successive firing times of the individual elements, since in that case the distances between the individual elements and the point at which the beam is desired to be focused are proportionally greater.

The control of the time of firing of the individual transducer elements is performed by system console equipment 24 responsive to operator commands provided by keyboard 26; for example, the desired focusing distance may be varied responsive to the user's requirements. Further details of system console equipment generally useful in connection with the practice of the invention disclosed herein may be found in commonly—assigned Fife et al U.S. Pat. No. 5,269,307, the teachings of which are incorporated herein by reference. However, the present invention is not to be limited thereby.

It will thus be appreciated that by properly controlling the sequence of firing of the individual elements of each of the subsets of the array, the beam can be focused at any desired depth in the structure. In typical image formation practice, the individual subsets of elements will each be fired several times with differing relative time delays such that structures spaced different distances from the array are successively in focus, i.e., such that structure at a number of different depths is imaged. The reflected energy is then displayed responsive to its time of receipt, such that a complete line is built up. The process is then repeated with respect to each subset of elements across the transducer to build up a complete image line-by-line. This entire process is repeated, typically at the 30 hz scan rate of typical video displays, such that the display is updated in real time.

As discussed above, typically ultrasonic transducers are designed such that the beam is as thin as possible in the plane of the image, that is, in the plane of FIG. 3, so as to provide maximum resolution in that plane. In that case, multiple element linear array transducers can be operated as above to cause beams of energy emitted by subsets of the elements to be focused, and the reflected energy can be used according to the skill of the art to form a B-scan ultrasonic image as discussed above.

The transducer must then be moved physically, typically perpendicular to the plane (that is, vertically with respect to the plane of FIG. 3) in order that a sequence of such images of cross sectional "slices" can be formed. An operator is then required to mentally interpolate these images to form a three-dimensional mental image of the interior of the structure.

According to the invention, subsets of the elements of the transducer are similarly controlled to fire at intervals of time, again such that the emitted beam is effectively focused at a desired distance from the transducer in the plane of FIG. 3. However, rather than be controlled to be as thin as possible in the plane of FIG. 3, as normally required by the prior art in order to provide an image of a cross-sectional slice through the object, the beam emitted by each of the elements according to the invention diverges in the direction perpendicular to the plane of FIG. 3. Therefore, rather than be reflected only at interfaces within a thin "slice" of the object, structure within a substantial volume of the object is illuminated with and reflects ultrasonic energy according to the invention. FIG. 5 shows one embodiment of a transducer according to the invention wherein each transducer element is provided with a lens to emit such a diverging beam, while FIGS. 6, 7, and 8 illustrate the manner in which the diverging beam is employed according to the invention to provide a three-dimensional image of structures in the volume of the object. Further embodiments of transducers providing diverging beams are discussed below.

FIG. 5 shows a transducer assembly 50 comprising a single row of transducer elements 52 in partial cross section, and illustrates one of the transducer elements 52 in contact with an object 60 to be imaged, such as an organ. A lens 62 of a material chosen for its relative acoustic impedance with respect to the typical acoustic impedance of the object 60 is disposed over the piezoelectric transducer element 52.

A typical piezoelectric transducer element 52 emits a generally planar wave when excited by an appropriate drive signal. In accordance with Snell's law, when such a wave transits an interface between materials having differing acoustic velocities, the path of the wavefront makes an angle at the interface. More specifically, when the ultrasonic wavefront passes from a relatively harder material, in which the speed of sound is relatively high, into a softer material in which the speed of sound is relatively low, the direction of propagation of the wave in the second medium is bent toward the normal to the interface; the amount of bending is described by Snell's law, just as Snell's law describes the bending of light waves in air when they encounter glass or water. Accordingly, in order to provide a diverging beam, it is simply necessary to provide a convex lens 62 of a material wherein the speed of sound is faster than in the material of the object 60. A convex lens of a polyetherimide, such as that sold as ULTEM by General Electric, or dimethyl pentene polymer, e.g., that sold as TPX by Westlake Plastics, Lenni, Pa., is suitable for most medical ultrasonic applications. In that case, when the acoustic energy passes from the lens 62 into the object 60 it forms a diverging beam. A concave lens of a material having a slower velocity of sound might alternatively be employed; the latter technique for transmitting a diverging beam of ultrasonic energy is disclosed by the Entrekin et al. paper and patent referred to above. The transducer may also be designed to emit a diverging beam by forming a convex external surface on the transducer elements.

Figure 13:
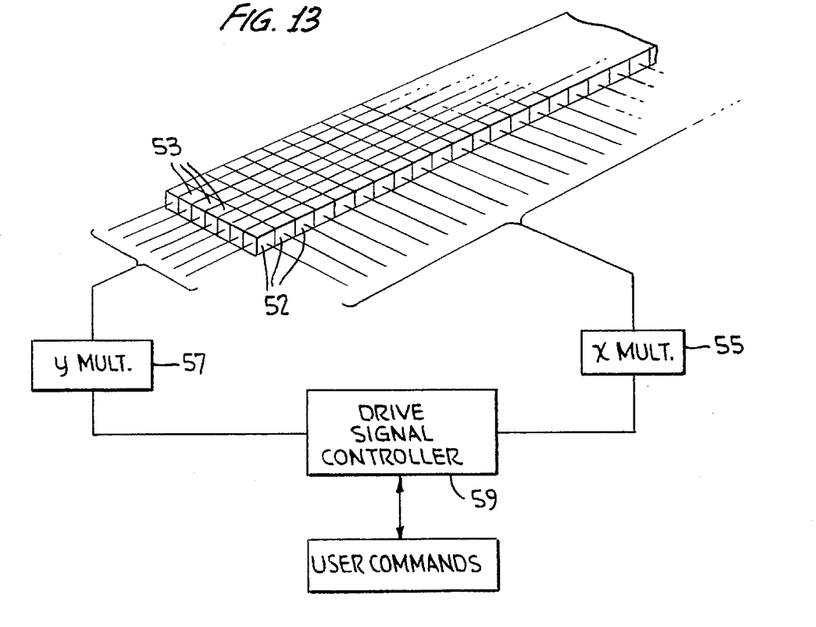
FIG. 13 shows a perspective view of a two-dimensional transducer array and associated circuit elements.

In a further embodiment, the single transducer element 52 shown in FIG. 5 may be replaced with a plurality of individually excited subelements 53; see FIG. 13. In the FIG. 13 embodiment, the individual subelements 53 may be fired at closely spaced intervals controlled such that the beams emitted by the subelements 53 are summed to yield a resultant beam diverging in the plane transverse to the array. To accomplish divergence in the transverse plane while focusing the beam in the longitudinal plane including the axis of elongation of the transducer, it may be convenient to employ x- and y- multiplexers 55 and 57 respectively controlled by a drive signal controller 59 responsive to operator commands for determining the divergence of the beam in the transverse plane and the depth of focus in the longitudinal plane.

Each of these alternatives is to be understood to be included where reference is made herein to a transducer emitting a beam diverging in the transverse plane. The Entrekin et al. patent also recognizes these possible methods for forming a diverging beam; see col. 5, line 54 through col. 6, line 29.

As noted, according to one aspect of the present invention, the ultrasonic energy is emitted in a diverging pattern as illustrated by the angle $\alpha$ shown in FIG. 5, such that energy is reflected from structure lying within a substantial volume of the object 60. In the prior art (apart from the Entrekin et al. paper and patent, as noted), ultrasonic transducers have been normally designed so as to reduce the angle $\alpha$ as close to zero as possible, i.e., so that the beam is as thin as possible, increasing the resolution of the cross-sectional "slices" thus generated. By comparison, according to the invention, beams of ultrasonic energy focused at desired distances from the transducer array in the plane of elongation of the array and diverging in the orthogonal plane are provided.

FIGS. 6–8 explain the manner in which three-dimensional information is generated responsive to energy reflected from objects within a volume of an object to be imaged according to the invention. For simplicity, reference is made in this discussion to beams as if emitted from single ones of the elements of the transducer arrays. However, it should be understood that in each case such reference is intended to refer to sequences of beams focused at differing distances from each of plural subsets of such elements, as discussed above in connection with FIG. 3.

FIG. 6 illustrates one preferred pattern of ultrasonic energy as if emitted by corresponding ones of transducer elements 16 forming parallel arrays 12 and 14. As noted above, in fact each of these elements is normally excited in sequence as part of a number of subsets of elements; the net effect is that a number of elements 16 successively emit beams 32 of ultrasonic energy which constructively interfere so as to be focused in the x direction, at several different depths z, while diverging in the y direction, that is, perpendicular to the direction of elongation of the arrays, as shown in FIG. 6.

In the embodiment shown, the transducer assembly 10 may comprise two parallel arrays 12 and 14 of elements 16 arranged such that diverging beams 32 of energy emitted by the corresponding elements of both arrays overlap in a triangular region 34; region 34 accordingly defines the region S that is effectively imaged according to the invention. The "waist" of the resultant beam 32, that is, its minimum thickness in the x dimension, at each focal distance (determined as described above by the sequence of firing the elements of each of the subsets of elements), is controlled to be sufficient to ensure that the focused beams from adjoining subsets of the transducer elements overlap slightly at the selected focal distance, so that all reflecting structure in adjacent regions 34 is detected.

FIGS. 7 and 8 illustrate the method of the invention as used to image the interior structure of an organ O having a tumor T therein; more specifically, FIGS. 7 and 8 illustrate location of the tumor T within O according to the invention. In FIG. 7, a transducer assembly as in FIG. 6 is juxtaposed to O, such that energy from corresponding transducer elements 16 of two parallel arrays of elements can be efficiently transmitted into O, while FIG. 8 is a cross-section taken along line 8—8 of FIG. 7. As indicated in FIG. 7, location of T within O in the displacement or x direction, that is, along transducer assembly 10, is performed by emitting energy from subsets of the elements 16 and detecting reflection thereof from T. The displacement of T is identified by detection of energy reflected therefrom by an element 16; detection by a single element is sufficient to determine the displacement x because the beam is focused so as to be narrow in the x dimension, as illustrated in FIGS. 3 and 6.

Location of T in the elevation or y and azimuth or z dimensions is accomplished by triangulation, that is, by comparison of the distances between two spaced transducer elements and a common reflecting point P on T, as illustrated in FIG. 8. The time-of-flight of ultrasonic pulses between the corresponding transducer elements 16 of each of the parallel arrays 12 and 14 and the common reflecting point P are measured and divided by the velocity of sound within O, providing values for the distances $r_1$ and $r_2$ between the respective transducer elements 16 and P. If the transducer elements 16 are spaced by equal distances a from the image plane I, the elevation y of reflecting point P and its azimuth z are described by the following simple equations:

$$r_1^2 = z^2 + (y-a)^2$$

$$r_2^2 = z^2 + (y+a)^2$$

As these two equations contain two measured quantities, $r_1$ and $r_2$, they can be solved for two dependent variables, y and z. With the value for x having been determined as above, the "reflector" P is located in three dimensions. The same process is then repeated for all identified reflectors P within S; this information is then used to provide an image of the reflectors within S, illustrating the structure within S.

Thus, according to one aspect of the invention, a transducer assembly is provided comprising two parallel arrays of transducer elements, each emitting defocused beams of energy into an overlapping region. This embodiment of the invention is particularly advantageous in that reflecting points within that region can thus be located in three dimensions without mechanical motion of the transducer, allowing formation of the three-dimensional image in real time. Providing the two arrays in a single assembly also simplifies correlation of the reflected energy signals detected by the individual elements of the two arrays, because the spatial relationships of the individual transducer elements of the arrays are fixed. However (and as discussed in detail below in connection with FIGS. 10A–E, 11, and 12), it should be understood that it is also within the scope of the invention to employ a transducer comprising a single array of elements to illuminate the same region of the object from different locations, i.e., after motion of the array from one location to the other, and also to employ transducers mechanically linked to move together. It is also possible to perform multiple identical steps of emitting energy and detecting reflected energy with respect to each of the elements, to increase the signal-to-noise ratio of the detected signals, in addition to firing the transducer elements of each subset at successive times to provide differing focal distances.

Several methods of forming a visible image displaying three-dimensional information are contemplated according to the invention. In a first embodiment of the invention, two visible images corresponding to data obtained as above concerning reflectors within a volume of an object to be imaged may be generated by algebraic manipulation of the information corresponding to two closely-spaced viewpoints, so as to exhibit parallax, whereby depth information is detectable by viewing the images by a viewer's two eyes separately. These two visible images can then be displayed simultaneously for stereoscopic viewing or may be displayed alternatingly while the viewer is provided with means ensuring that each of the viewer's eyes sees only the corresponding image.

More specifically, given the information concerning the displacement of the reflectors defining the structure of the object to be imaged in three dimensions derived as above, it is then possible to provide two visible images of that structure differing from one another such as to exhibit parallax corresponding to two closely-spaced viewpoints, e.g., corresponding to the position of the viewer's eyes. If these two images are then displayed such that each of the viewer's eyes only sees the corresponding image, whether this is done by simultaneous stereoscopic display of two images with crossed polarizers, or the like, or by alternating display of the first and second images with similar means for ensuring that the images are seen only by the correct eyes, the viewer can be provided with three-dimensional information.

For example, the two images may be formed with respect to image plane I in FIG. 2 from two view points spaced a viewing distance from I in the y dimension and spaced laterally from one another in the x dimension. In this case, the viewer would effectively look into the volume S as if in the orientation shown in FIG. 2. However, according to an important aspect of the invention, the viewpoint is not constrained to that or any other particular position.

According to another aspect of the invention, three-dimensional data concerning the position of the reflectors with respect to the arrays termed a "virtual image" can be stored, e.g., in a three-dimensional data array. Such a virtual image would store the positions of the reflectors with respect to an arbitrary image plane, for example, an image plane I extending between the two parallel arrays, as shown in FIG. 8, optionally together with other relevant information, such as their "brightness" i.e., reflectivity to ultrasonic energy. The viewer may then arbitrarily choose a desired viewpoint, for example, in order to view the reflecting structure from different sides or from different distances, or with overlying structure removed from the image. Storage of the data in the virtual image form provides computational simplicity and, in particular, makes it convenient for an image processing computer system storing a virtual image to be interfaced with a variety of display devices, including both stereoscopic devices, as discussed above, or devices wherein the three-dimensional information is displayed on a single screen depicting the reflecting structure within the object differently depending on its displacement from the image plane, thus providing visual depth clues for communicating three-dimensional structural information to the viewer.

According to this aspect of the invention, data determined as above locating reflecting points P within S with respect to the arbitrary image plane I is preferably stored as a three-dimensional "virtual image." Two images may then be formed by projecting a common reflector onto left and right stereo views, that is, to provide two images exhibiting parallax. The virtual image may then be employed for subsequent generation of visible images corresponding to a different image plane, so that the user can view the structure from a different direction, if desired, or from a different distance, or with overlying structure removed.

Those of skill in the art will recognize that automation of the process of generating a visible image as described above includes the step of identifying reflecting points P for comparison of the distances between P and the corresponding elements 16 of arrays 12 and 14, in order to determine x, y, and z for each P. Identification of such reflecting points P can be performed using any of a variety of methods known to the prior art; for example, the Ledley patents discussed above teach differentiation of a "reflection profile" to identify peaks therein, i.e., measuring the rate of change of the reflectivity of reflectors in a B-scan "slice" image to locate the most pronounced points thereon. Such a technique could be of use in locating common reflecting points, i.e., for correlating the reflector data detected using the elements of one of the transducer arrays to that detected employing the second of the arrays. Other known techniques might also or additionally be employed.

In this connection, it should be appreciated that the sequence of processing reflection data recorded with respect to each of the elements of an array in a first position to identify reflectors in the common volume prior to identifying the same reflectors with respect to an array in a second position, followed by comparing the two sets of identified reflectors to determine the actual location of the reflectors by triangulation, as above, is considered equivalent, for purposes of the present invention, to a processing sequence in which reflected signals recorded with respect to the corresponding elements of the arrays are compared to one another to locate common reflectors by triangulation prior to formation of a complete image.

In a further possible embodiment, "back-projection" techniques comparable to those employed for tomographic examination, i.e. CAT scans and the like, may be employed. In implementation of back-projection techniques for three-dimensional ultrasonic imaging according to the invention, ultrasonic energy is transmitted into the structure to be imaged from a large number of locations in a plane, and reflected energy is collected at the same or additional locations in the plane. Because the transmitted beam diverges in the plane, the direction of the reflector with respect to the transducer elements is not directly determined. According to so-called back-projection techniques, the reflected energy collected at each location may be displayed as a circular reflection profile (of radius determined by the time-of-flight of the energy between emission and detection) centered about the corresponding detector location. When energy reflected by a particular reflector is detected by a number of detectors, the circles displayed intersect. The points of intersection thus appear brighter on a display; if a sufficient number of sources and detectors are employed, the intersection points effectively merge to locate the reflecting structure in the plane. (The same process can be carried out mathematically, i.e. avoiding the display step per se.) Positions of the reflecting structure thus located can be processed to define the location of the reflectors with respect to an image plane. If similar information is then similarly collected with respect to a number of parallel planes, this information can be used according to the invention to generate an image displaying three-dimensional information.

Figure 9:
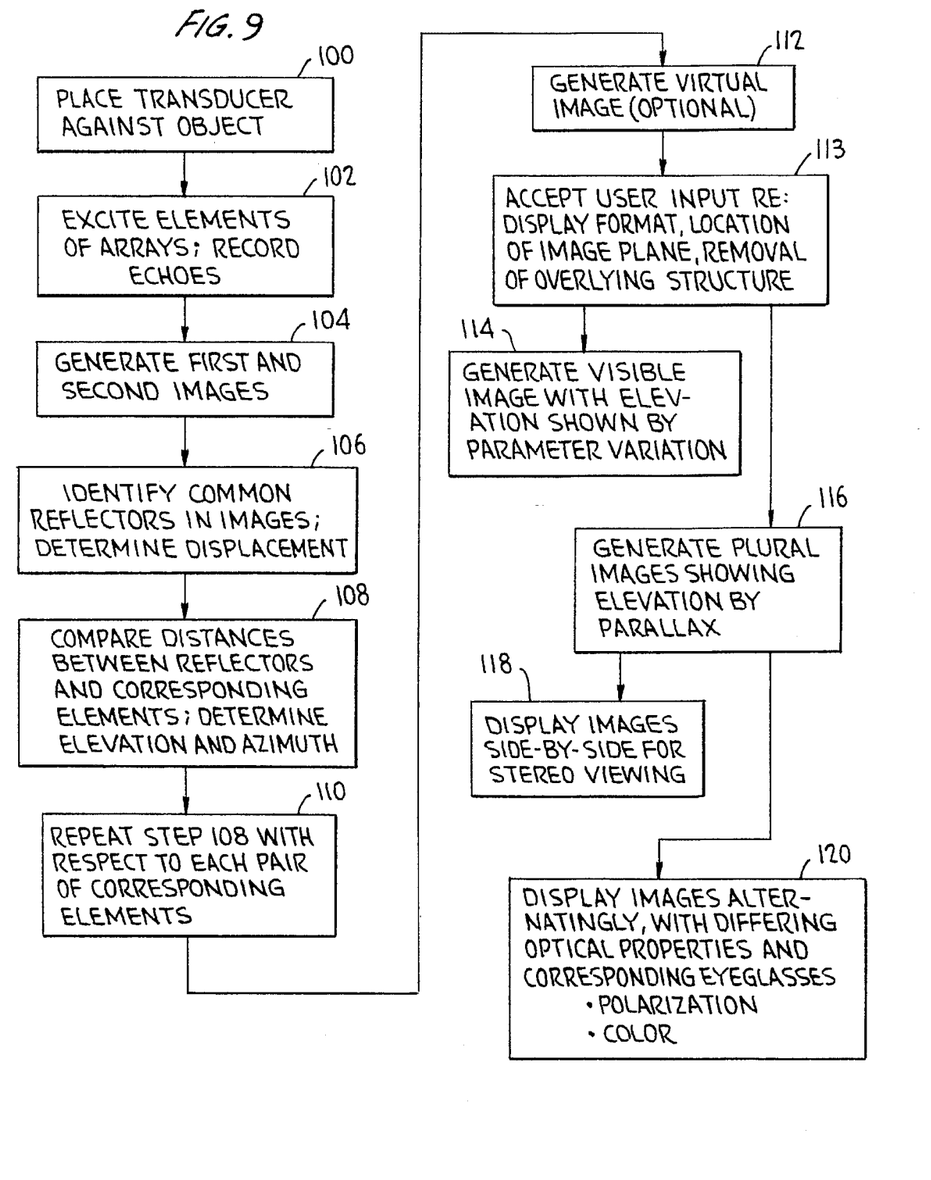
FIG. 9 is a flowchart illustrating the principal steps in formation of a three-dimensional image employing ultrasonic energy according to the invention.

FIG. 9 provides a schematic flowchart of the steps in formation of a true three-dimensional image of the interior of an object according to the invention. It should be appreciated that other and additional methods might also be employed without departure from the invention, as FIG. 9 is exemplary only.

Thus, at 100, a transducer according to the invention—for example, a transducer assembly comprising at least two parallel arrays of individual transducer elements—is placed in effective energy-transmitting relationship with an object to be imaged, such that energy is emitted into a common volume of the object from at least two spaced transducer locations. At 102, suitable drive signals are applied to subsets of the elements of both the transducer arrays, such that sequences of beams of ultrasonic energy, focused in a plane including the array (as shown in FIG. 3) and diverging in the orthogonal plane (as shown in FIG. 6), are emitted, the net effect being that wedge-shaped beams of ultrasonic energy, as illustrated in FIG. 6, are emitted. Echoes, that is, energy reflected from interfaces between materials of differing acoustic impedance within the object to be imaged, are detected by the same or different transducer elements, and are recorded for subsequent processing by system console equipment 24. In this example, this processing begins at 104 with generation of first and second "images" corresponding to the energy detected by the elements of the first and second transducer arrays.

It should be appreciated that because the elements of the transducer arrays each effectively emit a wedge-shaped beam, defocused in the plane perpendicular to the array, as compared to the focused or "pencil" beams emitted by typical prior art ultrasonic imaging transducers, the "images" formed in step 104 do not correspond directly to the A- or B-scan images formed by such prior art transducers. More particularly, according to the invention, and as depicted in FIG. 3, the elements of the array effectively emit wedge-shaped beams having substantial extent in the y and z dimensions, while being limited to a narrow thickness in the x dimension. The "images" formed in step 104 correspond to energy reflected from points within a region having substantial thickness in y and z, that is, the direction of the reflector from the transducer is not fixed. Accordingly, these "images" cannot be directly displayed as a cross-sectional view of a slice into the object, as in the "B-scan" prior art. The "images" thus formed in step 104 according to the invention correspond to the images shown by Entrekin et al; as acknowledged by Entrekin et al, if such images are displayed, motion cues or the like are needed in order to visibly resolve ambiguities therein.

Stated differently, the "images" formed in step 104 are ambiguous regarding the position of the reflectors with respect to the transducer position in the y and z dimensions; triangulation, performed by correlation of common reflectors in the images formed by the two transducer arrays, as described with reference to FIG. 8, is required to locate the reflectors in order to generate the three-dimensional data, and to generate a correct image.

By comparison, because the beam emitted by each subset of elements is focused in the plane of the array, as discussed above in connection with FIG. 3, the width of the beam effectively emitted by each element approximates the width of the element in the x dimension. Accordingly, there is no ambiguity in the x dimension, and the displacement of a particular reflector can be determined from reflected energy detected by either of the corresponding elements of the two arrays. Alternatively, and preferably, the redundancy in displacement information, that is, in the location of a reflector in the x dimension, can be employed to ensure correct identification of common reflectors, i.e., of points reflecting energy detected by elements of both arrays.

Therefore, in step 106, common reflectors, that is, structural features reflecting ultrasonic energy within the object to be imaged, are identified in the first and second images, locating them in the x dimension, determining their displacement (see FIG. 7). Next, at step 108, the distances between the corresponding elements in the arrays and common reflectors within the object are compared to locate the common reflectors in the y and z dimensions, determining their elevation and azimuth, respectively.

These steps are repeated, as indicated at 110, until common reflectors appearing throughout the extent of the region S of the object have been identified. The data concerning the position of the reflectors can be used as described below in connection with steps 114–120 to generate any of several types of visible display.

More specifically, if it is desired simply to form a visible image corresponding to the image plane I extending between parallel arrays of transducers, as in FIG. 6, two images exhibiting parallax can be generated in step 116, for stereoscopic viewing. When the image plane corresponds to or is parallel to I, the images exhibiting parallax can be generated by depicting the foreground structure displaced laterally more than background structure, proportional to the elevation y of the reflector. As discussed in detail below in connection with steps 118 and 120, the two images can then be displayed side-by-side, for simultaneous stereoscopic viewing, or alternatingly with means for ensuring that each of the viewer's eye sees only the correct image.

In an optional intermediate step 112, a "virtual image" may be generated, storing data corresponding to the displacement, azimuth and elevation of each of the identified reflectors within S; that is, the virtual image amounts to a three-dimensional array of data points corresponding to the internal volume of S, indicating the location of reflecting points therein. The virtual image may also store information responsive to the reflectivity or "brightness" of each of the reflectors. This virtual image forms a "database" used in subsequent steps for generating a visible image of the internal structure of S.

Generation of the virtual image is not necessary in every implementation of the methods of the invention, but is anticipated to be a convenient means of organizing the data stored responsive to detection of energy reflected from various structural features within the object to be imaged. The virtual image is anticipated to be particularly useful in convenient variation of the location of the desired image plane with respect to the sources and detectors of ultrasonic energy and in permitting the convenient interfacing of a class of transducer assemblies, each optimized in response to a particular anatomical situation, to a class of display devices, each offering different capabilities.

More specifically, the virtual image stores data defining the location of features to be imaged with respect to an arbitrary image plane; when the user selects a desired image plane for display of the visible image, or instructs the image display device to remove overlying structure (i.e., structure disposed between the transducer and structure of interest) from the image, the data stored in the virtual image are selected and recalculated responsive to the spatial relationship between the arbitrary and selected image planes.

Further, it is envisioned that the invention may have applicability to a wide class of ultrasonic imaging problems, many in the medical field. Different anatomical structures to be imaged may require different transducer designs, several of which are shown schematically in FIGS. 10A–E, 11, and 12 (discussed further below). As thus shown, while an assembly of two elongated arrays of transducer elements as discussed above simplifies the data processing required to form the image (since the positional relationship of the two arrays is fixed by the structure of the probe assembly), the invention will also be useful with other transducer structures. In order to simplify interfacing of the various types of transducers used in various data collection sequences, it may prove desirable to define a standard format for processing and storing three-dimensional data resulting from ultrasonic examination of a common volume of an object to be imaged. Various multiple-array transducer assemblies or single-array transducer assemblies used at differing locations to gather reflection data from a common imaged volume S, might then be supplied with suitable interface hardware and software to convert the reflector data signals to the standard format for analysis and display.

The virtual image discussed above, e.g., wherein the location of reflectors in an imaged volume S in the x, y, and z dimensions with respect to a reference image plane is stored, optionally together with their relative reflectivity or brightness, is one possibility for such a standard data storage format. Data stored in such a standard format could then be conveniently processed for analysis and display, accommodating a wide variety of display options. For example, in addition to display of three-dimensional images on either one or a pair of conventional video displays as discussed above, the image could be printed, or could be provided to a so-called "virtual reality" headset display worn by a surgeon. Storage of the data in a defined format would substantially simplify interfacing a variety of transducers to a variety of display devices.

The process of employing information stored in the virtual image to provide a visible image depicting three-dimensional information showing the shape of interfaces between materials of varying acoustic impedance within S, and thus showing the internal structure of S, may be carried out according to several techniques identified in FIG. 9, as well as other techniques not specifically identified therein, without departure from the present invention.

The choice of display technique to be employed may be determined in response to user input, as indicated at step 113. At the same time, other display parameters may be selected. For example, it is known to provide user-selectable "rotation" of an image, to permit viewing an object from different viewpoints; similar processing techniques can be employed to permit the viewer to select the desired image plane with respect to which the reflectors are displayed in the visible image according to the invention.

According to one aspect of the invention, not all of the data concerning reflecting points within the object to be imaged need be displayed in every image provided. For example, commonly the surgeon will be constrained by anatomy to place the transducer against the outer surface of an organ, or the like, but will be primarily interested in structure some distance into the organ. According to the invention, the image may be displayed showing structure disposed between "near-field" and "far-field" planes within the object to be imaged. Selection of the distance of the "near-field" plane effectively allows dissection of any structure overlying the structure of particular interest. Storing all the data concerning the reflectors within the object in a virtual image database as discussed above is envisioned to be a particularly convenient method of allowing the overlying structures to be deleted from the image, while allowing the viewpoint to be effectively selected by the user, as described above. If the overlying structure is deleted incrementally in successive display steps, the effect would be to gradually remove layers of the overlying structure.

In general, the problem of providing a visible image conveying three-dimensional information is a problem of differentiating foreground and background information—that is, depicting objects closer to the viewer differently than those further from the viewer. Preferably, this is done in a manner mimicking the way in which three-dimensional information is perceived in ordinary viewing. For example, if one looks across a landscape of substantial depth, one perceives distant objects more dimly colored, less distinctly outlined, and smaller than closer objects. Therefore, according to one display technique provided by the invention, a single visible image may be provided, wherein the depiction of particular reflectors varies responsive to their elevation with respect to the image plane, thus conveying three-dimensional information.

A first display possibility is accordingly indicated at step 114, whereby a single visible image conveying variation in elevation of the structure by parameter variation is generated and displayed. A single display device 28 (FIG. 1) displaying a single image thus exhibiting parameter variation corresponding to the elevation of reflectors with respect to the image plane would effectively convey three-dimensional information to the viewer. For example, background structure can be depicted as less bright and with less contrast than foreground structure. Similarly, foreground structure may be outlined in the display more heavily than background structure. Background structure might similarly be depicted relatively smaller than foreground structure; however, this option is less useful in medical applications, since the viewer has no visible clues to provide scale to the display, and because disease may distort the sizes of structure appearing in the display.

As discussed above, three-dimensional information is also perceived by perception of parallax, that is, by subconscious analysis of the differing images provided by one's eyes by virtue of their horizontal spacing. Essentially, "parallax" refers to the fact that, in comparison of images taken at separated viewpoints, foreground objects are displaced from one another more than background objects. This fact is widely used to provide three-dimensional images in two-dimensional media; for example, common stereoscopic viewers comprise means for simultaneously displaying two images taken at closely-spaced locations (corresponding to the spacing of the viewer's eyes) together with means for ensuring that each eye "sees" only the corresponding image.

To depict three-dimensional information according to the invention using the mind's ability to synthesize such information from parallax, two images are generated at step 116. As noted above, parallax is provided in the two images by laterally displacing objects from one another in the two images by an amount proportional to their elevation with respect to the image plane, that is, such that foreground objects are laterally displaced more than background objects also appearing in the two images. More specifically, where the viewpoint is as shown in FIG. 2, and referring to the algebraic definition for the elevation y given there, if the elevation y of particular reflecting structure is negative, that structure is in the background, and the reflector may be imaged in substantially the same position in both images; where y is positive, the reflector should be in the foreground. Accordingly, the reflectors should be displaced laterally outwardly proportionally to y in the two images, to provide the proper relative parallax.

The two images exhibiting parallax may then be displayed side-by-side simultaneously for stereoscopic viewing, as at 118. The stereoscopic images may be also be displayed alternatingly on a single display, if means are provided to ensure that each of the viewer's eyes sees only the corresponding image. For example, as indicated by step 120, the images may be displayed with alternating polarization, and the viewer provided with crossed-polarizer eyeglasses 30 (FIG. 1). Essentially similar effects can be provided by color filtration of the images, with appropriately-colored filters in the eyeglasses, or by providing individual shutters between the viewer's eyes and the display, synchronized to the alternating display of the images exhibiting parallax.

It will also be appreciated that the "parameter variation" and "parallax" techniques described above for providing three-dimensional perception in two-dimensional images can be combined for even greater accuracy of perception of the imaged structure.

Figure 10A:
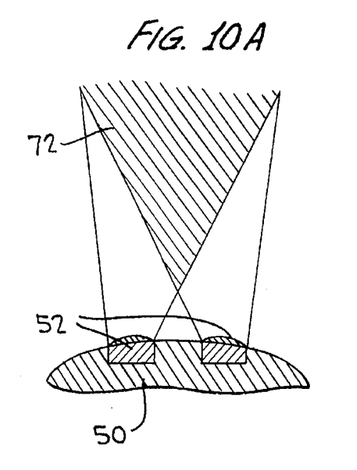
FIGS. 10A–C illustrate various arrangements of the transducer arrays as used according to the invention, in views corresponding to FIG. 8.
Figure 10B:
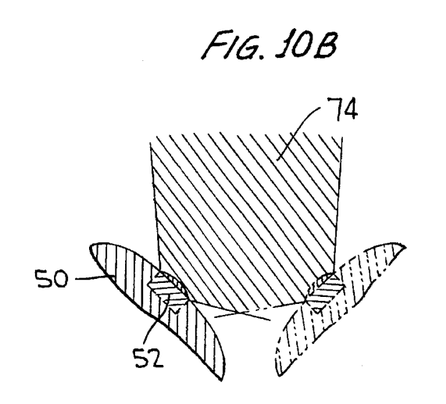

FIGS. 10A–E show schematically various arrangements of arrays of transducer elements according to the invention. FIG. 10A is generally comparable to the arrangement shown in FIG. 6 as above; that is, a pair of elongated arrays of transducer elements 52 are disposed parallel to one another at the surface of a transducer assembly 50, such that wedge-shaped beams of energy emitted in the plane transverse to the direction of elongation of the arrays overlap in a region 72 as shown. In FIG. 10B, the transducer surfaces are at an angle of approximately 90 degrees to one another, so that the overlapping region 74 is defined by their lateral spacing. Further, as indicated by depiction of one of the transducer assemblies 50 in phantom in FIG. 10B, it is to be understood that the first image may be formed by a transducer assembly 50 in the position shown at the left in FIG. 10B, and a second image formed some time later, that is, after having moved the transducer assembly to the position shown on the right. Correlation of the two images to determine the elevation of common reflectors in the object, that is, analyzing the data to identify common reflectors, would then require data concerning the relative position of the transducers at the time the data were recorded.

Figure 10C:
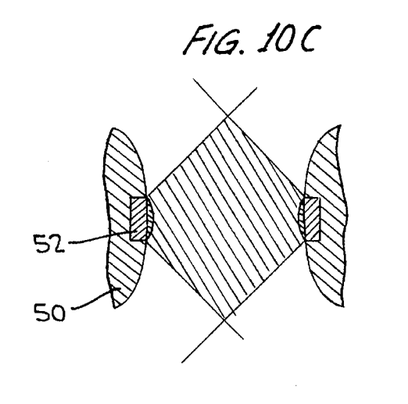

Similarly, as shown in FIG. 10C, the transducer assembly may be disposed first on one side and then the other of a region of an object to be imaged. Again, this could be accomplished by two transducer assemblies simultaneously, or by the same assembly operated at intervals of time, after movement from one position to the other.

Figure 10D:
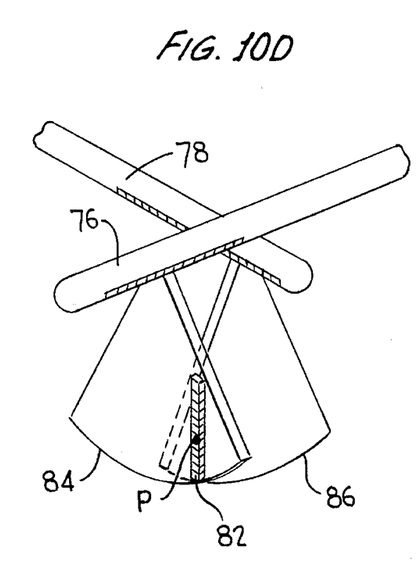
FIG. 10D shows a perspective view of a further possible arrangement of the transducer arrays according to the invention.

FIG. 10D shows a further embodiment of the invention wherein the arrays of transducer elements are not parallel to one another but are crossed, each emitting a sequence of wedge-shaped beams as indicated into an object. A transducer assembly of this type would be convenient, for example, in examining an organ from an accessible surface. In this case, a reflector P would be located in two dimensions by virtue of the fact that the common volume 82 shared by any two of the wedge-shaped beams 84, 86 emitted by arrays 76, 78 is columnar in shape. Hence, a reflector would be located in a columnar volume 82 common to orthogonal scanning planes 84, 86 by identification of the two corresponding scanning steps. Location of P in the third dimension—that is, identifying its distance within volume 82 from the plane including the transducer arrays 76 and 78—would be performed by dividing the time of flight of the reflected energy from P to either transducer by the speed of sound in the object.

Figure 10E:
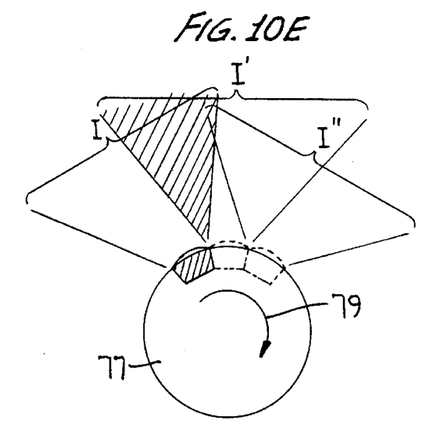
FIG. 10E illustrates a further embodiment of the invention in a view corresponding to FIGS. 10A–C.

FIG. 10E reflects the fact that a single transducer assembly 77 rotatable about its axis as indicated by arrow 79 could be used in forming a series of angularly-spaced sequential images. Reflectors appearing in overlapping pairs of imaged volumes I, I', I", and so on could be identified and their distance from the corresponding angular positions of the transducer determined, generally as above, as the transducer is rotated. Three-dimensional information concerning the structure of the object being imaged could then be derived. Reflected energy detected by such a rotatable transducer assembly might be particularly suitable for reflecting locations by back-projection, as above.

Figure 11:
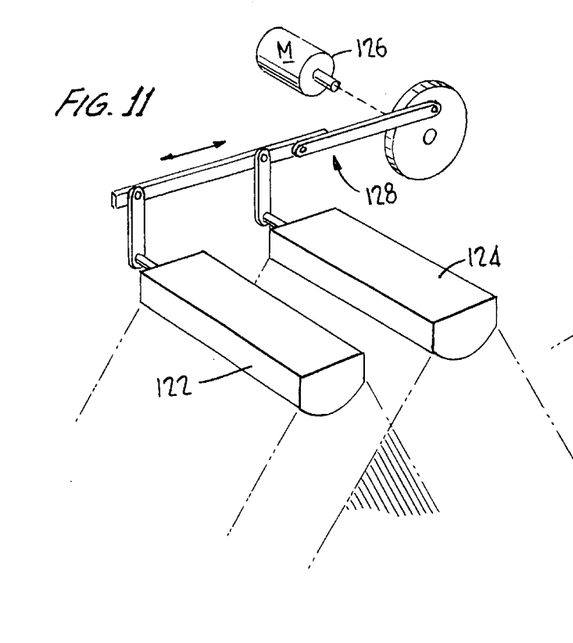
FIGS. 11 and 12 show respectively perspective and end views of a further embodiment of a two-transducer probe according to the invention.
Figure 12:
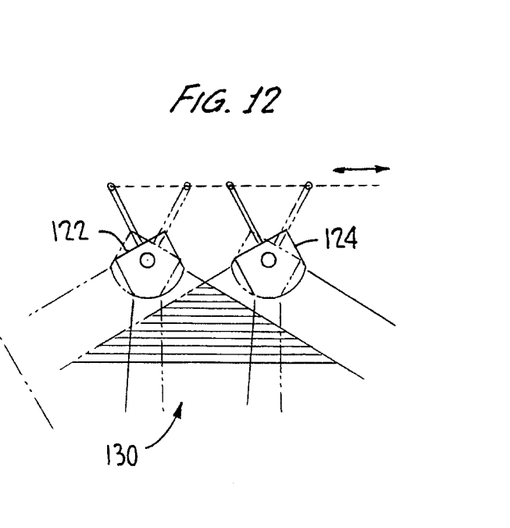

FIGS. 11 and 12 show respectively perspective and end views of a pair of parallel spaced elongated transducers adapted to oscillate about parallel axes. In this embodiment, the two transducers 122 and 124, both typically comprising elongated arrays of individually excitable elements, are mounted for oscillatory motion about axes parallel to the directions of elongation of the transducers. The oscillation of the transducers 122 and 124 may be driven by a motor 126 connected to the transducers through a linkage, shown generally at 128. Mechanically driving the transducers in this manner allows a relatively large volume 130 of an object to be imaged by ultrasonic energy emitted by the transducers 122 and 124. In order to prevent interference of the transducers with the object, it may be preferable to enclose the transducer assembly in a sealed container having a sound-transmitting wall in contact with the object to be imaged; the interior of the container would be filled with a sound-transmitting fluid, such as a mineral oil or the like.

It should also be understood that while elongated arrays of transducer elements extending along a straight line have been described, in certain circumstances it may also be useful to similarly employ curved, elongated transducer arrays, e.g. having an array of transducer elements extending around the rounded tip of a probe, to more closely fit objects of particular configuration.

The invention having thus been described in detail, it is useful to summarize the distinctions of the invention with respect to the prior art.

As noted above, by far the prevalent prior art practice in ultrasonic imaging has been to generate a series of cross-sectional "slices" i.e., B-scan images, and to display these in sequence, such that a skilled practitioner can mentally "see" three-dimensional structure in the object. In so forming cross-sectional "slices" the aim of the art has been to transmit a narrow beam into the object, to minimize ambiguity in the location of structure reflecting the energy.

The Entrekin et al. disclosures discussed above proceed contrary to this aspect of the typical prior art practice, in that Entrekin et al. provide a diverging beam, such that energy is reflected from structure within a wedge-shaped volume of the object. As acknowledged by Entrekin et al, this leads to ambiguity in the displayed image.

The present invention also employs the diverging-beam transducer structure proposed by Entrekin et al. However, according to the invention, at least two arrays of such transducers are disposed at spaced locations (or a single transducer array is moved between the spaced locations), such that structure within a common volume of the object reflects ultrasonic energy; the locations of the common reflectors are then determined by triangulation of distance information derived by comparison of the two images, so that the image provided correctly represents this "true" three-dimensional information. Entrekin et al. show no such processing steps.

The Smith et al. and von Ramm et al. papers discussed above describe a system whereby a two-dimensional array of transducers is employed to provide a so-called "C-scan" that is to allow imaging of a slice through the structure parallel to the plane of the surface of the object. This also allows overlying structure to be removed from the image. Von Ramm et al. simply display two images exhibiting parallax side-by-side for stereoscopic viewing, or false-coloring reflector data in accordance with its time of receipt. Again, as in the case of the Entrekin et al. disclosures, von Ramm et al. do not teach determination of the reflectors' actual location by triangulation as a step in the generation of the image to be displayed. More specifically, von Ramm et al. do not propose analysis of reflection data obtained with respect to at least two different transducer array locations to locate common reflectors, and processing of the reflection data to yield a true three-dimensional image, as performed according to the invention.

The Ledley U.S. Pat. Nos. 4,747,411 and 4,821,728 discussed above (insofar as understood) propose generation of three-dimensional images by identification of reflectors on angularly-spaced B-scan "slices". The reflectors are identified by peaks in the reflectivity, and are located in three dimensions by the respective line in a B-scan, by the location of the scanning plane, and by the distance from the source to the reflector. The reflectors are then projected onto image planes corresponding to two spaced image locations, to provide three-dimensional information to the viewer. Ledley teaches neither location of reflectors by triangulation of common reflectors in data detected by transducers at spaced locations, nor the employment of diverging ultrasonic beams.

Further according to the invention, the sources and detectors are not constrained to lie in the image plane; the effective viewpoint defined by the image plane may be located at any desired position, independent of the location of the sources and detectors. Thus, although in one preferred embodiment of the invention discussed above, the image plane extends between the parallel arrays, simplifying the processing of the reflected energy to form the visible image, this is not critical to the invention. By comparison, prior art three-dimensional ultrasonic imaging techniques all involve plural images formed at viewpoints fixed with respect to the source and detector locations, constraining the user's view of the objects to be imaged.

Finally, it will be appreciated that while a number of different embodiments of the invention have been described in detail, these are exemplary only, and that the invention encompasses many additional modifications and improvements, which will be apparent to those of skill in the art. Therefore, the above disclosure of the invention should not be read to limit its scope, which is limited only by the following claims.

What is claimed is:

1. A method for formation and display of three-dimensional images of the structure of objects employing ultrasonic energy, comprising the steps of:

providing at least one ultrasonic transducer assembly comprising a plurality of transducer elements for emitting ultrasonic energy and being capable of detecting ultrasonic energy, said elements being adapted to emit beams of ultrasonic energy diverging in at least one plane;

operating said at least one array to transmit ultrasonic energy from at least two spaced locations into a common region of an object to be imaged, and to detect energy reflected from structure in said region;

analyzing the detected energy in order to determine the position of structure reflecting energy detected by said elements at said spaced locations, in three dimensions; and generating and displaying a visible image including three-dimensional information responsive to the determined position of the structure.

2. The method of claim 1, wherein said step of analyzing the detected energy in order to determine the position of structure reflecting energy is performed by examining the reflected energy to identify common reflecting points in said structure, and measuring differential spacing of said common reflecting points from elements detecting energy reflected therefrom.

3. The method of claim 2, wherein said step of identification of common reflecting points is performed by back-projection of reflected energy.

4. The method of claim 2, wherein said step of determining the position of structure reflecting energy is performed by triangulation of the common reflecting points from at least two elements detecting energy reflected therefrom, as a function of the relative position of the at least two elements.

5. The method of claim 4, wherein said at least two elements are corresponding elements of parallel elongated arrays of said elements.

6. The method of claim 5, wherein said parallel elongated arrays are provided as part of a unitary transducer assembly.

7. The method of claim 1, wherein said elements are adapted to emit beams of ultrasonic energy diverging in at least one plane by being provided with lens means of a material exhibiting a selected ultrasonic velocity.

8. The method of claim 1, wherein said elements are adapted to emit beams of ultrasonic energy diverging in at least one plane by being divided into subelements, said subelements being actuated to emit ultrasonic energy at respective times such that a resultant beam of ultrasonic energy diverging in said at least one plane is emitted.

9. The method of claim 1, wherein said step of generating a visible image is carried out so as to generate two images including differing relative parallax information in accordance with said position of said identified structure, responsive to the elevation of said identified structure with respect to a selected image plane.

10. The method of claim 9, wherein said two images are displayed alternatingly on a single display device, and wherein means are provided such that each eye of a viewer sees only one of said images.

11. The method of claim 10, wherein said means provided such that each eye of a viewer sees only one of said images comprises means for differentially polarizing the images intended to be seen by each eye, and polarization filter means adapted to be disposed between the viewer's eyes and the display device.

12. The method of claim 10, wherein said means provided such that each eye of a viewer sees only one of said images comprises means for differential color filtration of the images intended to be seen by each eye, and color filter means adapted to be disposed between the viewer's eyes and the display device.

13. The method of claim 9, wherein said step of displaying is carried out by displaying said two images for simultaneous stereoscopic viewing.

14. The method of claim 1, wherein said step of displaying is carried out by displaying a single visible image including said three-dimensional information.

15. The method of claim 14, wherein said three-dimensional information is provided in a single visible image by differentially depicting identified structure therein with respect to the relative elevation of said identified structure.

16. The method of claim 15, wherein said step of differentially depicting identified structure in a single visible image is performed by varying parameters of the display responsive to the relative elevation of the identified structure with respect to a selected image plane.

17. The method of claim 16, wherein the parameters varied with respect to the relative elevation of the identified structure depicted in the image include one or more of the relative brightness, color, contrast, outline density, or size thereof.

18. The method of claim 1, wherein said elements of said transducer assembly are arranged along a line, and each element of said transducer array emits ultrasonic energy in a generally wedge-shaped pattern, such that said beams of energy emitted by said elements diverge in a plane generally perpendicular to said line.

19. The method of claim 18 wherein said transducer assembly comprises a pair of spaced parallel elongated transducer arrays, each said array comprising a plurality of individual transducer elements, such that the energy emitted by corresponding elements of said pair of arrays overlaps to define said common region.

20. The method of claim 19, wherein said visible image is generated and displayed with respect to an image plane including a line centered between said spaced parallel elongated transducer arrays.

21. The method of claim 1, wherein said step of generating a visible image of the identified structure including information responsive to the determined elevation of said identified structure includes the steps of generating a virtual image including information responsive to the relative position of said identified structure with respect to an arbitrary image plane, and processing positional information included in said virtual image to generate at least one visible image including positional information of said identified structure with respect to a selected image plane for display.

22. The method of claim 21 wherein said step of processing positional information included in said virtual image comprises the step of recalculating said positional information included in said virtual image with respect to the spatial relationship between said arbitrary and selected image planes.

23. The method of claim 1, wherein said elements of said transducer assembly are arranged along a line, and comprising the step of operating subsets of said elements in sequence to emit beams of energy focused at a selectable distance from said transducer assembly in a first plane including said line, and said beams diverging in the orthogonal plane.

24. The method of claim 1, wherein said step of determining the position of the identified structure in three dimensions is performed by determining the respective distances between the identified structure and said corresponding elements at said spaced locations detecting energy reflected from said identified structure, and calculating the actual position of the identified structure from the determined respective distances and the respective positions of the corresponding elements.

25. A method of forming three-dimensional images of structures employing ultrasonic energy, comprising the steps of:

providing at least one elongated array of individually excitable transducer elements, each element of said array being operable to emit a sequence of generally wedge-shaped beams of ultrasonic energy focused in a plane including the direction of elongation of the array and diverging in the plane perpendicular thereto in response to an excitation signal, and said elements being capable of detecting return of ultrasonic energy after reflection from said structure;

disposing said at least one array at spaced locations with respect to an object the internal structure of which is to be imaged, such that the beams of energy emitted by corresponding elements of said array are transmitted from said spaced locations into a common portion of the object;

operating subsets of the elements of the array to transmit beams of ultrasonic energy from said spaced locations into the object, and to detect reflection of ultrasonic energy from energy-reflecting structure within the corresponding portion of the object at said spaced locations;

locating common reflecting structure from which reflected energy is detected by corresponding elements at said spaced locations;

determining the distance from each element to the common reflecting structure within the corresponding portion of the object;

comparing the distances between said identified common structure and said corresponding elements in each of said arrays, to determine the relative location of said identified common structure with respect to an image plane; and generating and displaying a visible image including three-dimensional information responsive to the relative location of said identified common features.

26. The method of claim 25, wherein said step of identification of common reflecting points is performed by back-projection of reflected energy.

27. The method of claim 25, wherein said step of determining the position of structure reflecting energy is performed by triangulation of the common reflecting points from at least two elements detecting energy reflected therefrom, as a function of the relative position of the at least two elements.

28. The method of claim 25, wherein two said elongated arrays are provided as part of a single transducer assembly, and wherein said arrays are disposed parallel to one another.

29. The method of claim 25, wherein said step of generating a visible image including three-dimensional information is carried out by generating and displaying two images including differing relative parallax information in accordance with the relative location of said identified common features of said structure.

30. The method of claim 29, wherein said two images are displayed alternatingly on a single display device, and wherein means are provided such that each eye of a viewer sees only one of said images.

31. The method of claim 29, wherein said step of displaying is carried out by displaying said two images on two separate display devices for simultaneous stereoscopic viewing.

32. The method of claim 25, wherein said step of displaying is carried out by displaying a single visible image including three-dimensional information.

33. The method of claim 25, wherein said step of generating and displaying a visible image including information responsive to the relative elevation of said identified common features is performed by generating a virtual image comprising data locating said features with respect to an arbitrary image plane, accepting user input responsive to selection of a desired image plane, and processing the data of the virtual image to generate a visible image relative to said desired image plane.

34. The method of claim 25, wherein said elements are adapted to emit beams of ultrasonic energy diverging in at least one plane by being provided with lens means of a material exhibiting a selected ultrasonic velocity.

35. The method of claim 25, wherein said elements are adapted to emit beams of ultrasonic energy diverging in at least one plane by being divided into subelements, said subelements being actuated to emit ultrasonic energy at respective times such that a resultant beam of ultrasonic energy diverging in said at least one plane is emitted.

36. A method of generating a three-dimensional visible image of internal structure of an object, comprising the steps of:

providing a transducer assembly comprising at least one elongated array of a number of individually excitable transducer elements, said array being operable to emit a series of beams of ultrasonic energy focused at a predetermined distance from the transducer assembly in a first plane, and diverging in the orthogonal plane, operating said array such that energy is transmitted into a common portion of the object from elements of said array at spaced locations, and detecting reflection of said energy from internal structure thereof at said spaced locations, comparing the reflection of energy by common features of said internal structure of said object as detected by elements at said spaced locations to determine the location of said features with respect to a first image plane, and generating and displaying an image of the internal structure of said object depicting the relative elevation of said features with respect to said first or a different image plane.

37. The method of claim 36, wherein said step of generating an image comprises the step of generating two images including differing relative parallax information in accordance with the relative elevation of said identified common features of said structure.

38. The method of claim 37, wherein said two images are displayed alternatingly on a single display device, and wherein means are provided such that each eye of a viewer sees only one of said images.

39. The method of claim 37, wherein said step of displaying is carried out by displaying said two images on two separate display devices for simultaneous stereoscopic viewing.

40. The method of claim 36, wherein said step of displaying is carried out by displaying a single visible image including three-dimensional information.

41. The method of claim 36, comprising the further step of employing the determined elevation of said features with respect to a first image plane to generate a virtual image including data locating said features with respect to an arbitrary image plane, and wherein said step of generating an image of the internal structure of said object depicting the relative elevation of said features with respect to said first or a different image plane comprises the steps of accepting user input defining a desired image plane and employing the data stored as said virtual image to generate a visible image of the internal structure of said object depicting the relative elevation of said features with respect to said desired image plane.

42. The method of claim 36, wherein said transducer assembly comprises two parallel arrays of individually excitable transducer elements.

43. Apparatus for generating and displaying a three-dimensional image of structure internal to an object, comprising:

an ultrasonic transducer assembly for disposition in juxtaposition to said object, said transducer assembly comprising at least one elongated transducer array comprising a plurality of individual transducer elements and being operable to emit a series of beams of ultrasonic energy focused at a selectable distance from the transducer assembly in a first plane and diverging in the orthogonal plane, said elements being capable of detecting ultrasonic energy, controller means connected to the elements of said array for supplying drive signals to excite the elements of the array in succession to emit overlapping beams of ultrasonic energy into a common region of said object, and said controller means comprising means for processing signals received from elements of at least one said array disposed at spaced locations responsive to detection of energy reflected from structure in said region in order to:

locate common features of the structure within a given portion of the object from which reflected energy is detected by corresponding elements in said array at said spaced locations;

determine the distance from said corresponding elements to the located common features of the structure;

compare the distances between identified common features of the structure and said corresponding elements to determine the relative elevation of said identified common features with respect to a first image plane; and generate a visible image including information corresponding to said relative elevation of said identified common features of the structure with respect to said first or a different image plane; and means for display of said visible image.

44. The apparatus of claim 43, wherein said visible image including information corresponding to said relative elevation of said identified common features of the structure comprises two images wherein the relative elevation of features is depicted by provision of relative parallax information.

45. The apparatus of claim 44, wherein said means for display comprises means for alternatingly displaying said images in combination with means for ensuring that each of a viewer's eyes sees only one of said images.

46. The apparatus of claim 45, wherein said means for display alternatingly displays said images with differing polarization or color content, and wherein said means for ensuring comprises corresponding polarization or color filtration means.

47. The apparatus of claim 45, wherein said means for display comprises means for simultaneously displaying said images for stereoscopic viewing thereof.

48. The apparatus of claim 43, wherein said information corresponding to said relative elevation of said identified common features of the structure is included in said visible image by differentially depicting said identified common features of the structure with respect to their relative elevation.

49. The apparatus of claim 48, wherein said identified common features of the structure are differentially depicted in a single visible image by varying parameters of the display, including one or more of the relative brightness, color, contrast, outline density, or size thereof, with respect to the relative elevation of the identified structure depicted therein.

50. The apparatus of claim 43, wherein said transducer assembly comprises two parallel elongated arrays of individually excitable transducer elements.

51. The apparatus of claim 50, wherein said first image plane includes the direction of elongation of said arrays.

52. The apparatus of claim 51, wherein said image is derived such that said image plane extends between said parallel arrays.

53. The apparatus of claim 43, wherein said controller means comprises means for analyzing said reflected energy in order to generate a virtual image of the interior of the object to be imaged, including data responsive to the relative elevation of the identified common features of the structure with respect to an arbitrary image plane, and said controller means further comprises means for accepting user input for selecting a desired image plane, and wherein said means for processing is further capable of processing the data stored as said virtual image as a function of the relationship of the desired and arbitrary virtual image planes.

54. The apparatus of claim 43, wherein said transducer assembly comprises lens means disposed between said transducer elements and the object to be imaged, said lens means being formed of a material and defining a shape such that said beam diverges in said orthogonal plane.

55. The apparatus of claim 43, wherein each said transducer array comprises a two-dimensional array of individually excitable transducer elements, and wherein said controller means is operable to supply drive signals to said elements such that the beams of ultrasonic energy emitted by groups of elements of said array are focused in one plane and divergent in the orthogonal plane.

56. The apparatus of claim 43, further comprising means for moving one or more of said arrays between said spaced locations with respect to an object the structure of which is to be imaged.

* * * * *